United States Patent
Wilson et al.

(10) Patent No.: US 9,663,477 B1
(45) Date of Patent: May 30, 2017

(54) SYNTHESIS AND STRUCTURE OF 3,5-DIAMINO-2,6-DI-(TERT-BUTYL-NNO-AZOXY) PYRAZINE AS A CRITICAL INTERMEDIATE IN THE SYNTHESIS OF A NOVEL ENERGETIC COMPOUND

(71) Applicants: Rebecca M. Wilson, Alexandria, VA (US); Joseph D. Mannion, Washington, DC (US); Jesse S. Moran, Alexandria, VA (US)

(72) Inventors: Rebecca M. Wilson, Alexandria, VA (US); Joseph D. Mannion, Washington, DC (US); Jesse S. Moran, Alexandria, VA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 101 days.

(21) Appl. No.: 14/121,568

(22) Filed: Sep. 19, 2014

(51) Int. Cl.
*C07D 241/20* (2006.01)
(52) U.S. Cl.
CPC ................... *C07D 241/20* (2013.01)
(58) Field of Classification Search
CPC .................................................. C07D 241/20
See application file for complete search history.

(56) References Cited

U.S. PATENT DOCUMENTS 3,814,752 A 6/1974 Maruyama et al.

OTHER PUBLICATIONS

Churakov, et al., Synthesis of [1,25]Oxadiazolo[3,4-e][1,2,3,4]tetrazine 4,6-Di-N-oxide, 1995, 5(6), 227-228, Mendeleev Commun., www.sciencedirect.com.

Tartakovsky, et al., Synthesis and structure of pyrldoannelated 1,2,3,4-tetrazine 1,3-dioxides, Nov. 2004, vol. 53, No. 11, pp. 2577-2583, Russian Chemical Bulletin, International Edition, Springer Science + Business Media, Inc.

*Primary Examiner* — Joseph Kosack
(74) *Attorney, Agent, or Firm* — Fredric J. Zimmerman

(57) ABSTRACT

The present disclosure relates generally to a critical intermediate in a synthesis of a postulated energetic material, and more specifically relates to a critical intermediate, 3,5-diamino-2,6-di-(tert-butyl-NNO-azoxy)pyrazine, having the structure:

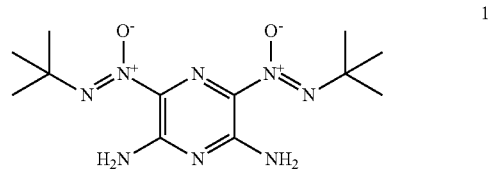

The postulated energetic material has calculated performance properties that greatly exceed those of HMX and CL-20. The specific critical intermediate (Compound 1) shown above has a molecular weight of 310.359 g/mol, a density at −123° C. of 1.293 g/mL, and a density at 20° C. of 1.259 g/mL.

11 Claims, 1 Drawing Sheet

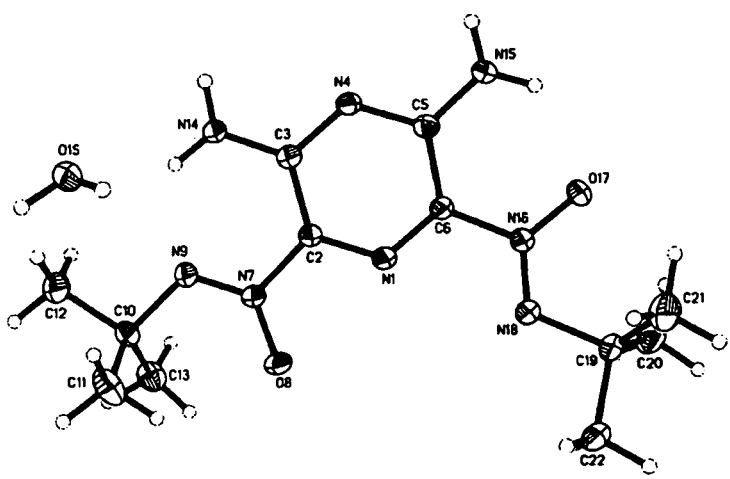

SYNTHESIS AND STRUCTURE OF 3,5-DIAMINO-2,6-DI-(TERT-BUTYL-NNO-AZOXY) PYRAZINE AS A CRITICAL INTERMEDIATE IN THE SYNTHESIS OF A NOVEL ENERGETIC COMPOUND

STATEMENT OF GOVERNMENT INTEREST

The present invention described herein may be manufactured and used by or for the Government of the United States of America for governmental purposes without the payment of any royalties thereon or therefore.

FIELD OF THE DISCLOSURE

The present invention relates generally to a critical intermediate in the synthesis of a postulated energetic material, and it relates to a critical intermediate having the general structure:

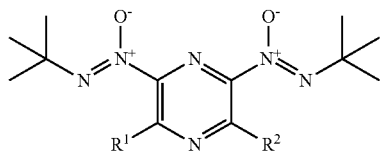

where $R^1=NH_2$, F, Cl, Br, I, OMe, or OEt and $R^2=NH_2$, F, Cl, Br, I, OMe, or OEt, and more specifically relates to 3,5-diamino-2,6-di-(tert-butyl-NNO-azoxy)pyrazine (1), having the structure:

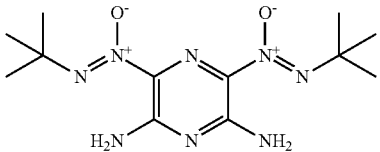

BACKGROUND OF THE DISCLOSURE

A postulated novel energetic compound, pyrazino[2,3-e:6,5-e']di[1,2,3,4]tetrazine 1,3,7,9-tetraoxide (PDTTO), is a high energy, high density material with a CO-level oxygen balance. Calculations for PDTTO indicate a greater energetic performance than existing nitramine high explosives, such as HMX or CL-20. For example, the calculated detonation pressure ($P_{CJ}$) of PDTTO exceeds that of CL-20 by 8%, and the calculated specific impulse ($I_{SP}$) of PDTTO is 9% greater than that of CL-20.

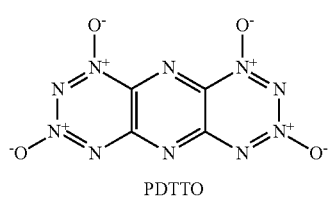

The critical intermediate of the present invention is an immediate precursor to PDTTO. The critical intermediate is synthesized via a multi-step protocol from commercially available 2,6-dichloropyrazine. There is a need for the development of a critical intermediate in the synthesis of an energetic material that exceeds the performance of currently available nitramine high explosives such as HMX or CL-20.

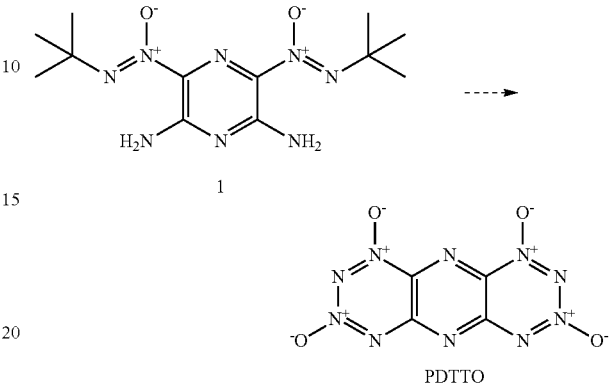

BRIEF SUMMARY OF THE DISCLOSURE

According to the present invention, there is provided a critical intermediate having the general structure:

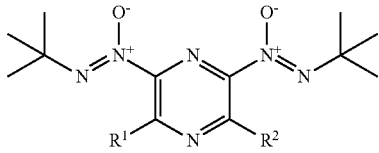

where $R^1=NH_2$, F, Cl, Br, I, OMe, or OEt and $R^2=NH_2$, F, Cl, Br, I, OMe, or OEt, and more specifically, 3,5-diamino-2,6-di-(tert-butyl-NNO-azoxy)pyrazine, having the structure:

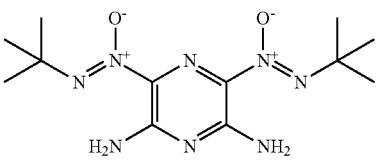

More particularly, the specific critical intermediate (Compound 1) shown above has a molecular weight of 310.359 g/mol, a density at −123° C. of 1.293 g/mL, and a density at 20° C. of 1.259 g/mL.

The critical intermediate of the present invention is synthesized from commercially available 2,6-dichloropyrazine (2) by nucleophilic substitution with sodium azide to give 5-azidotetrazolo[1,5-a]pyrazine (3; isomeric with 2,6-diazidopyrazine). The 5-azidotetrazolo[1,5-a]pyrazine is selectively reduced with sodium borohydride to form 5-aminotetrazolo[1,5-a]pyrazine (4). The 5-aminotetrazolo[1,5-a]pyrazine is dihalogenated with N-bromosuccinimide to form 2-amino-6-azido-3,5-dibromopyrazine (5), the amino group of which is oxidized to a nitroso group via a sulfilimine (6) and trapped with tert-butyldibromoamine to give 6-azido-3,5-dibromo-2-(tert-butyl-NNO-azoxy)pyrazine (7). The azide group of pyrazine 7 is selectively reduced with sodium borohydride to give 6-amino-3,5-dibromo-2-(tert-butyl-NNO-azoxy)pyrazine (8), and the resulting amino group of pyrazine 8 is oxidized to a nitroso group via a sulfilimine (3,5-dibromo-2-(tert-butyl-NNO-azoxy)-6-(S,S-dimethyl-sulfilimino)pyrazine, 9) and trapped with tert-butyldibromoamine to give 3,5-dibromo-2,6-di-(tert-butyl-NNO-azoxy)pyrazine (10). Diamination of pyrazine 10 results in 3,5-diamino-2,6-di-(tert-butyl-NNO-azoxy)pyrazine (1).

BRIEF DESCRIPTION OF THE DRAWING

The FIGURE is an X-ray crystal structure of 3,5-Diamino-2,6-di-(tert-butyl-NNO -azoxy)pyrazine (1) as a monohydrate.

DETAILED DESCRIPTION OF THE DISCLOSURE

In various exemplary embodiments, the present disclosure demonstrates that, in accordance with the process of the present invention, 3,5-diamino-2,6-di-(tert-butyl-NNO-azoxy)pyrazine (1), a critical intermediate in the synthesis of a novel energetic material, has been invented. The energetic material has calculated performance properties that greatly exceed those of HMX and CL-20.

Actual Synthesis:

The critical intermediate of the present invention was prepared from commercially available 2,6-dichloropyrazine (2), which was first converted to 5-azidotetrazolo[1,5-a] pyrazine (3; isomeric with 2,6-diazidopyrazine) by nucleophilic displacement with sodium azide as described in: Shaw, J. T.; Brotherton, C. E.; Moon, R. W.; Winland, M. D.; Anderson, M. D.; Kyler, K. S. *J. Heterocycl. Chem.* 1980, 17, 11. This 5-azidotetrazolo[1,5-a]pyrazine (3) was then selectively reduced to 5-aminotetrazolo[1,5-a]pyrazine (4) with sodium borohydride according to the above cited literature procedures.

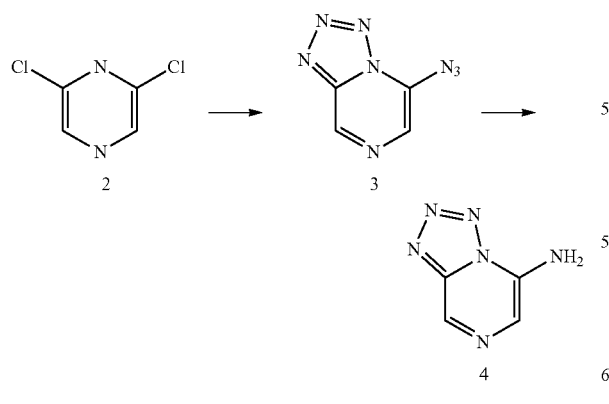

It is known that aminopyrazines can be directly halogenated with either bromine or chlorine; this chemistry was adapted to dibrominate 5-aminotetrazolo[1,5-a]pyrazine with NBS to give 2-amino-6-azido-3,5-dibromopyrazine (5) shown below:

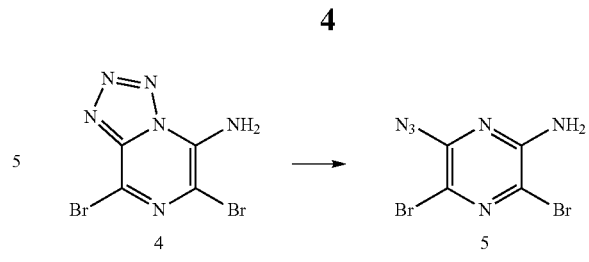

2-Amino-6-azido-3,5-dibromopyrazine (5)

To a round bottom flask with a stirbar was added 5-aminotetrazolo[1,5-a]pyrazine (2.15 g, 15.8 mmol, 1.0 equiv), dimethyl sulfoxide (63 mL, 0.25 M), and water (3.2 mL). The resulting solution was cooled to 10° C., and freshly recrystallized N-bromosuccinimide (8.43 g, 47.4 mmol, 3.0 equiv) was added portion-wise with stirring over 45 min while maintaining the reaction temperature between 10-15° C. The reaction was allowed to stir for an additional hour between 10-15° C., after which time water (200 mL) was added slowly until product precipitation ceased. The precipitate was collected by vacuum filtration, redissolved in diethyl ether, washed with water, dried over magnesium sulfate, and concentrated to give the title compound as a light-sensitive light yellow solid in 69% yield (3.22 g). Mp: 108-109° C. IR: 3480, 3300, 2119, 1600, 1534, 1511, 1437 cm$^{-1}$. $^1$H NMR (300 MHz, CDCl$_3$): δ 5.09 (br s, 1H). $^{13}$C{$^1$H} NMR (75 MHz, CDCl$_3$): δ 150.8, 147.4, 116.9, 112.6. DART-HRMS Calcd. for C$_4$H$_3$N$_6$Br$_2$ [M+H]$^+$: 292.8780. Found: 292.8766.

Formation of 6-azido-3,5-dibromo-2-(S,S-dimethylsulfilimino)pyrazine (6), oxidation of this material to a nitrosopyrazine (not shown), and in situ trapping with tert-butyldibromoamine gave 6-azido-3,5-dibromo-2-(tert-butyl-NNO-azoxy)pyrazine (7) in 67% yield over two steps:

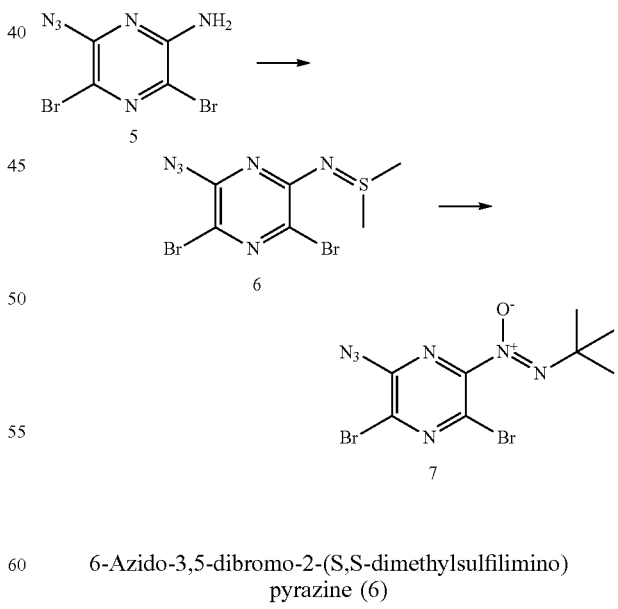

6-Azido-3,5-dibromo-2-(S,S-dimethylsulfilimino) pyrazine (6)

An oven-dried Schlenk flask was charged with 2-amino-6-azido-3,5-dibromopyrazine (588 mg, 2.00 mmol, 1.0 equiv) and anhydrous methylene chloride (12 mL) under argon, and the flask was wrapped in aluminum foil to protect the solution from light. A second oven-dried Schlenk flask was charged with anhydrous methylene chloride (13.3 mL, 0.15 M) and anhydrous dimethyl sulfoxide (417 mg, 5.33 mmol, 2.7 equiv) under argon. The solution was cooled to −78° C., and trifluoromethanesulfonic anhydride (1.13 g, 4.00 mmol, 2.0 equiv) was added dropwise via syringe, and the resulting reaction mixture was stirred at −78° C. for 10 min. The previously prepared solution of 2-amino-6-azido-3,5dibromopyrazine was then added to the reaction flask dropwise via syringe over approximately 5-10 min. This flask was covered with aluminum foil, and the reaction was stirred at −78° C. for 3.5 h, after which time the flask was allowed to warm slowly to −35° C. over 1 h. Concentrated aqueous ammonium hydroxide (15 mL) was added, the cold bath was removed, and the reaction was stirred for 15 min. Methylene chloride was added to dissolve the resulting bright yellow precipitate, and the layers were separated. The aqueous layer was extracted with methylene chloride (2×30 mL), and the combined organic layers were washed with water (2×30 mL), dried over magnesium sulfate, and concentrated. The title compound was obtained as 710 mg of a bright yellow powder and used immediately without further purification. $^1$H NMR (300 MHz, CDCl$_3$): δ 2.84 (s, 6H). $^{13}$C{$^1$H} NMR (75 MHz, CDCl$_3$): δ 157.9, 145.4, 124.3, 108.5, 32.9. DART-HRMS Calcd. for C$_6$H$_7$N$_6$SBr$_2$ [M+H]$^+$: 352.8814. Found: 352.8802.

6-Azido-3,5-dibromo-2-(tert-butyl-NNO-azoxy) pyrazine (7)

A solution of m-chloroperbenzoic acid (77% peroxide; 1.33 g, 5.93 mmol, 3.0 equiv) in methylene chloride (35 mL) in a round bottom flask with a stirbar was cooled to 4° C. Sulfilimine 6 (700 mg, 1.98 mmol, 1.0 equiv) was added over 5 min as a solution in methylene chloride (35 mL), and the reaction was stirred for 45 min at 4° C. in the dark, during which time large amounts of m-chlorobenzoic acid precipitated. tert-Butyldibromoamine (548 mg, 2.37 mmol, 1.2 equiv) was added as a solution in methylene chloride (5 mL), the cold bath was removed, and the reaction was allowed to stir for 14 h at 25° C. The resulting orange solution was washed with 1 M sodium carbonate (2×30 mL) and water (50 mL), dried over magnesium sulfate, and concentrated to give a bright orange oil. This crude product was chromatographed on silica (50% methylene chloride in hexanes) to yield the title compound as a light-sensitive, off-white crystalline solid in 67% yield over two steps (504 mg). Mp: 86-87° C. IR: 2160, 2127, 1496 cm$^{-1}$. $^1$H NMR (300 MHz, CDCl$_3$): δ 1.52 (s, 9H). $^{13}$C{$^1$H} NMR (75 MHz, CDCl$_3$): δ 149.6, 148.8, 128.5, 123.1, 61.2, 25.5. DART-HRMS Calcd. for C$_8$H$_{10}$N$_7$OBr$_2$ [M+H]$^+$: 377.9308. Found: 377.9300.

Selective reduction of 6-azido-3,5-dibromo-2-(tert-butyl-NNO-azoxy)pyrazine (7) with sodium borohydride gave 6-amino-3,5-dibromo-2-(tert-butyl-NNO-azoxy)pyrazine (8):

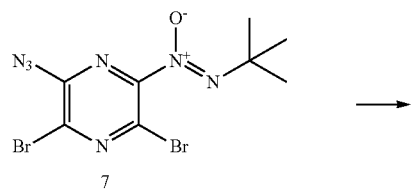

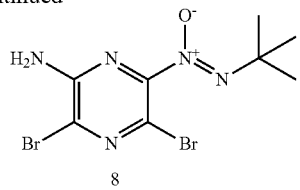

6-Amino-3,5-dibromo-2-(tert-butyl-NNO-azoxy) pyrazine (8)

In a darkened fume hood, a solution of 6-azido-3,5-dibromo-2-(tert-butyl-NNO-azoxy)pyrazine (800 mg, 2.11, 1.0 equiv) in ethanol (42 mL, 0.05M) in a round bottom flask with a stirbar was cooled to 4° C. Sodium borohydride (160 mg, 4.22 mmol, 2.0 equiv) was added portion-wise as a solid over 5 min, and the resulting suspension was stirred for 1 h at 4° C. The reaction was concentrated, and the solids were redissolved in diethyl ether (50 mL) and water (50 mL). The layers were separated, and the aqueous layer was extracted with diethyl ether (2×50 mL). The combined organic layers were washed with water (50 mL), dried over magnesium sulfate, and concentrated. The crude brownish-red solid was chromatographed on silica (methylene chloride) to provide the title compound as a purple crystalline solid in 68% yield (504 mg). Mp: 122-124° C. IR: 3473, 3331 cm$^{-1}$. $^1$H NMR (300 MHz, CDCl$_3$): δ 5.30 (br s, 2H), 1.50 (s, 9H). $^{13}$C{$^1$H} NMR (75 MHz, CDCl$_3$): δ 150.9, 150.4, 123.3, 114.0, 60.8, 25.5. DART-HRMS Calcd. for C$_8$H$_{12}$N$_5$OBr$_2$ [M+H]$^+$: 351.9403. Found: 351.9386.

From aminopyrazine 8, synthesis of 3,5-dibromo-2-(tert-butyl-NNO-azoxy)-6-(S,S-dimethylsulfilimino)pyrazine (9), subsequent oxidation (nitrosopyrazine not shown), and tert-butylazoxypyrazine formation (3,5-dibromo-2,6-di-(tert-butyl-NNO-azoxy)pyrazine, 10) were performed in a manner similar to the method described for compounds 5-7:

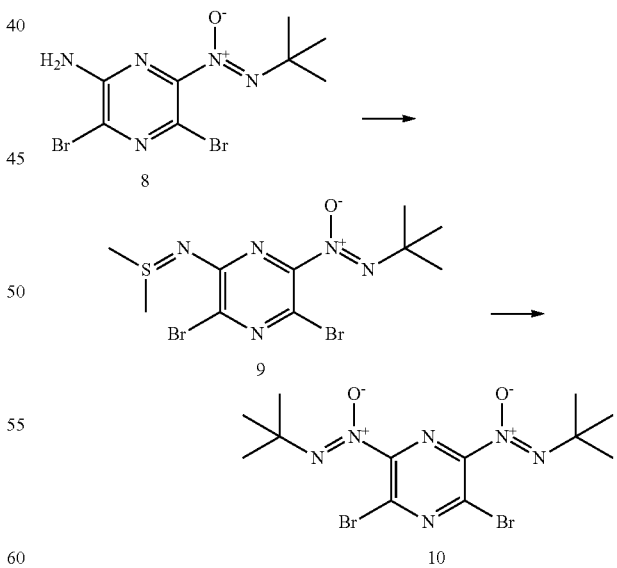

3,5-Dibromo-2-(tert-butyl-NNO-azoxy)-6-(S,S-dimethylsulfilimino)-pyrazine (9)

An oven-dried Schlenk flask was charged with 6-amino-3,5-dibromo-2-(tert-butyl-NNO-azoxy)pyrazine (585 mg, 1.66 mmol, 1.0 equiv) and anhydrous methylene chloride (9.8 mL) under argon, and the flask was wrapped in aluminum foil to protect the solution from light. A second oven-dried Schlenk flask was charged with anhydrous methylene chloride (11 mL, 0.15 M) and anhydrous dimethyl sulfoxide (302 mg, 3.87 mmol, 2.3 equiv) under argon. The solution was cooled to −78° C., and trifluoromethanesulfonic anhydride (818 mg, 2.90 mmol, 1.75 equiv) was added dropwise via syringe, and the resulting suspension was stirred at −78° C. for approximately 10 min. The previously prepared solution of 6-amino-3,5-dibromo-2-(tert-butyl-NNO-azoxy) pyrazine was then added to the reaction flask dropwise via syringe over approximately 20 min. This flask was covered with aluminum foil, and the reaction was stirred at −78° C. for 2 h and then allowed to warm to −40° C. over 2 h, after which point the cold bath was removed, and the reaction was allowed to warm to room temperature over 30 min. Concentrated aqueous ammonium hydroxide (25 mL) was added, and the reaction was stirred for 15 min. Methylene chloride (30 mL) was added, and the layers were separated. The aqueous layer was extracted with methylene chloride (2×30 mL), and the combined organic layers were washed with water (2×30 mL), dried over magnesium sulfate, and concentrated. The 3,5-dibromo-2-(tert-butyl-NNO-azoxy)-6-(S,S-dimethylsulfilimino)pyrazine was obtained as 529 mg (77% yield) of a bright yellow powder and used immediately without further purification. $^1$H NMR (300 MHz, CDCl$_3$): δ 2.86 (s, 6H), 1.49 (s, 9H). DART-HRMS Calcd. for C$_{10}$H$_{16}$N$_5$OSBr$_2$ [M+H]$^+$: 411.9437. Found: 411.9417.

3,5-Dibromo-2,6-di-(tert-butyl-NNO-azoxy)pyrazine (10)

A solution of m-chloroperbenzoic acid (77% peroxide; 861 mg, 3.84 mmol, 3.0 equiv) in methylene chloride (26 mL) in a round bottom flask with a stirbar was cooled to 4° C. 3,5-Dibromo-2-(tert-butyl-NNO-azoxy)-6-(S,S-dimethylsulfilimino)pyrazine (529 mg, 1.28 mmol, 1.0 equiv) was added over 5 min as a solution in methylene chloride (26 mL), and the reaction was stirred for 30 min at 4° C. in the dark, during which time large amounts of m-chlorobenzoic acid precipitated. tert-Butyldibromoamine (310 mg, 1.34 mmol, 1.05 equiv) was added as a solution in methylene chloride (1 mL), the cold bath was removed, and the reaction was allowed to stir for 14 h at 25° C. The resulting orange solution was washed with 1 M sodium carbonate (2×30 mL) and water (30 mL), dried over magnesium sulfate, and concentrated to give a bright orange oil. This crude product was chromatographed on silica (8% ethyl acetate in hexanes) to yield the 3,5-dibromo-2,6-di-(tert-butyl-NNO-azoxy)pyrazine as an off-white solid in 73% yield (408 mg). IR: 1491 cm$^{-1}$. $^1$H NMR (CDCl$_3$, 300 MHz): δ 1.51 (s, 18H). $^{13}$C{$^1$H} NMR (75 MHz, CDCl$_3$): δ 149.1, 130.5, 61.5, 25.5. DART-HRMS Calcd. for C$_{12}$H$_{19}$N$_6$O$_2$Br$_2$ [M+H]$^+$: 436.9931. Found: 436.9937.

Amination of 3,5-dibromo-2,6-di-(tert-butyl-NNO-azoxy)pyrazine (10) with concentrated ammonium hydroxide provided the critical synthetic intermediate, 3,5-diamino-2,6-di-(tert-butyl-NNO-azoxy)pyrazine (1):

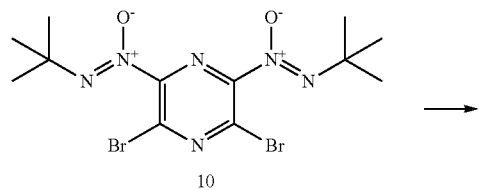

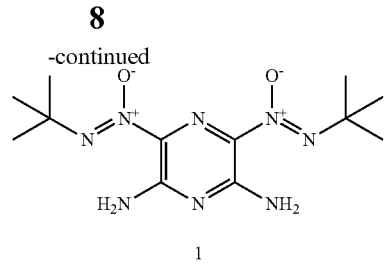

3,5-Diamino-2,6-di-(tert-butyl-NNO-azoxy)pyrazine (1)

3,5-Dibromo-2,6-di-(tert-butyl-NNO-azoxy)pyrazine (312 mg, 0.712 mmol) was suspended in concentrated aqueous ammonium hydroxide (10 mL), sealed in a glass pressure vessel, and heated at 50° C. for 2 h. The reaction was cooled to 25° C., and methylene chloride (10 mL) and water (10 mL) were added. The layers were separated, and the aqueous layer was extracted with methylene chloride (2×10 mL). The combined organic layers were washed with water (3×10 mL), dried over magnesium sulfate, and concentrated. The crude product was chromatographed on silica (40% ethyl acetate in hexanes) and recrystallized from diethyl ether to give 3,5-diamino-2,6-di-(tert-butyl-NNO-azoxy)pyrazine as a light yellow crystalline solid in 41% yield (90.0 mg). The X-ray crystal structure of this material showed 1 as a monohydrate as indicated in the FIGURE.

Mp: 71-73° C. IR: 3400, 3145, 1609, 1543, 1479, 1431 cm$^{-1}$. $^1$H NMR (300 MHz, CDCl$_3$): δ 1.48 (s, 18H). $^{13}$C{$^1$H} NMR (75 MHz, CDCl$_3$): δ 149.0, 125.8, 59.6, 26.2. DART-HRMS Calcd. for C$_{12}$H$_{23}$N$_8$O$_2$ [M+H]$^+$: 311.1939. Found: 311.1932.

In another alternative exemplary embodiment, the critical intermediate may have one or more of the following variations in structure:

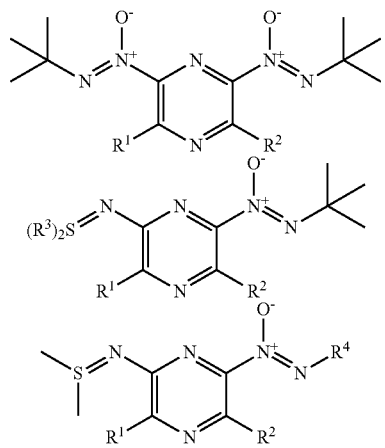

Further, R$^1$ and R$^2$ are individually selected from amines or leaving groups. The leaving group is selected from the group consisting of at least one of F, Cl, Br, I, NH$_2$, OMe, OEt, or the like. R$^3$ is selected from the group consisting of an alkyl or aryl, and R$^4$ is selected from alkyl or acyl.

Although the present disclosure has been illustrated and described herein with reference to exemplary embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

Finally, any numerical parameters set forth in this Specification and the attached Claims are approximations (for example, by using the term "about") that may vary depending upon the desired properties sought to be obtained by the present invention. At the very least, and not as an attempt to limit the application of the doctrine of equivalents to the scope of the Claims, each numerical parameter should be construed in light of the number of significant digits and by applying ordinary rounding.

What is claimed is:

1. A critical intermediate having the formula, comprising:

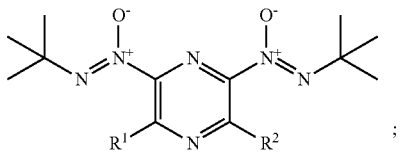

wherein $R^1$ and $R^2$ are amines or leaving groups, wherein the leaving group is selected from the group consisting of F, Cl, Br, I, OMe, OEt, and the like.

2. The critical intermediate according to claim 1, wherein $R^1$ and $R^2$ are amino groups.

3. The critical intermediate according to claim 1, wherein the critical intermediate has a molecular weight between about 300 to about 440.

4. The critical intermediate according to claim 1, wherein the critical intermediate has a density of 1.293 when measured at −123° C.

5. The critical intermediate according to claim 1, wherein the critical intermediate has a density of 1.259 when measured at 20° C.

6. The critical intermediate according to claim 1, wherein the critical intermediate has a formula weight is between about 200 to about 600.

7. A critical intermediate having the structure:

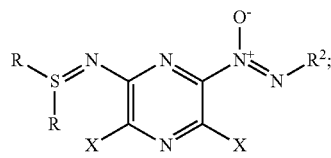

wherein each X is selected from at least one of $NH_2$, F, Cl, Br, I, OMe, and OEt; wherein each R is an alkyl or aryl group; and wherein $R^2$ is an alkyl or acyl group.

8. A process for the preparation of a critical intermediate, comprising:

providing 2,6-dichloropyrazine;

converting the 2,6-dichloropyrazine to 5-azidotetrazolo[1,5-a]pyrazine (3) by nucleophilic displacement with sodium azide;

selectively reducing the 5-azidotetrazolo[1,5-a]pyrazine with sodium borohydride to form 5-aminotetrazolo[1,5-a]pyrazine;

dihalogenating 5-aminotetrazolo[1,5-a]pyrazine to form 2-amino-6-azido-3,5-dibromopyrazine;

conversion of 2-amino-6-azido-3,5-dibromopyrazine to 6-azido-3,5-dibromo-2-(S,S-dimethylsulfilimino)pyrazine;

oxidizing the 6-azido-3,5-dibromo-2-(S,S-dimethylsulfilimino)pyrazine to a nitrosopyrazine, and trapping of this nitrosopyrazine with tert-butyldibromoamine to form 6-azido-3,5-dibromo-2-(tert-butyl-NNO-azoxy)pyrazine;

selective reduction of 6-azido-3,5-dibromo-2-(tert-butyl-NNO-azoxy)pyrazine with sodium borohydride to 6-amino-3,5-dibromo-2-(tert-butyl-NNO-azoxy)pyrazine;

conversion of 6-amino-3,5-dibromo-2-(tert-butyl-NNO-azoxy)pyrazine to 3,5-dibromo-2-(tert-butyl-NNO-azoxy)-6-(S,S-dimethylsulfilimino)pyrazine;

oxidizing the 3,5-dibromo-2-(tert-butyl-NNO-azoxy)-6-(S,S-dimethylsulfilimino)-pyrazine to a nitrosopyrazine, and trapping of this nitrosopyrazine with tert-butyldibromoamine to form 3,5-dibromo-2,6-di-(tert-butyl-NNO-azoxy)pyrazine; and diaminating 3,5-dibromo-2,6-di-(tert-butyl-NNO-azoxy)pyrazine resulting in 3,5-diamino-2,6-di-(tert-butyl-NNO-azoxy)pyrazine.

9. The process of preparing the critical intermediate of claim 8, wherein halogenated means brominated.

10. The process of preparing the critical intermediate of claim 8, wherein halogenated means chlorinated.

11. The process of preparing the critical intermediate of claim 8, further comprising suspending the 3,5-diamino-2,6-di-(tert-butyl-NNO-azoxy)pyrazine in a concentrated solution of aqueous ammonium hydroxide.

* * * * *